United States Patent [19]
Colliot et al.

[11] Patent Number: 5,877,194
[45] Date of Patent: Mar. 2, 1999

[54] COMBINATIONS OF A FUNGICIDE CONTAINING AN AZOLE GROUP WITH AN INSECTICIDE CONTAINING A PYRAZOLE, PYRROLE OR PHENYLIMIDAZOLE GROUP

[75] Inventors: Francois Colliot, Fontaines Saint Martin; Jean-Marie Gouot, St Cyr Au Mont D'Or; Francis Molle, Villeurbanne; Patrice Duvert, Lyons, all of France

[73] Assignee: Rhone-Poulenc Agrochimie, Lyon Cedex, France

[21] Appl. No.: 953,318

[22] Filed: Oct. 17, 1997

Related U.S. Application Data

[63] Continuation of Ser. No. 640,828, filed as PCT/FR94/01254 filed Oct. 27, 1994, abandoned.

[30] Foreign Application Priority Data

Nov. 4, 1993 [FR] France ................................. 93 13400
Sep. 14, 1994 [FR] France ................................. 94 11214

[51] Int. Cl.⁶ ......................... A01N 43/56; A01N 43/64
[52] U.S. Cl. ..................... 514/383; 514/404; 514/407
[58] Field of Search ................................. 514/404, 407, 514/383

[56] References Cited

U.S. PATENT DOCUMENTS

| | | | |
|---|---|---|---|
| 4,731,385 | 3/1988 | Tsuboi et al. | 514/789 |
| 5,177,098 | 1/1993 | Benoit | 514/399 |
| 5,200,421 | 4/1993 | Ludwig et al. | 514/383 |
| 5,232,940 | 8/1993 | Hatton et al. | 514/407 |
| 5,246,953 | 9/1993 | Greiner et al. | 514/383 |
| 5,256,683 | 10/1993 | Hutt et al. | 514/383 |
| 5,290,791 | 3/1994 | Greiner et al. | 514/383 |
| 5,380,743 | 1/1995 | Hutt et al. | 514/399 |
| 5,385,926 | 1/1995 | Ludwig et al. | 514/383 |

FOREIGN PATENT DOCUMENTS

| | | |
|---|---|---|
| 0018943 | 11/1980 | European Pat. Off. . |
| 0019581 | 11/1980 | European Pat. Off. . |
| 0295117 | 12/1988 | European Pat. Off. . |
| 0370905 | 5/1990 | European Pat. Off. . |
| 0378953 | 7/1990 | European Pat. Off. . |
| 0460940 | 12/1991 | European Pat. Off. . |
| 0467791 | 1/1992 | European Pat. Off. . |
| 0467792 | 1/1992 | European Pat. Off. . |
| 0484165 | 5/1992 | European Pat. Off. . |
| 0510458 | 10/1992 | European Pat. Off. . |
| 0545834 | 6/1993 | European Pat. Off. . |
| 0548759 | 6/1993 | European Pat. Off. . |
| 91/01640 | 2/1991 | WIPO . |

OTHER PUBLICATIONS

*The Pesticide Manual*, ed. C. Tomlin, British Crop Protection Council, England, tenth edition, pp. 463 and 1033 (1994).

*The Pesticide Manual*, ed. C. Tomlin, British Crop Protection Council, England, eleventh edition, pp. 545–547 and 1258–1259 (1997).

Colliot et al, Brighton Crop Protection Conference—Pests and Diseases—1992, 2–1, pp. 29–34 (Conference dates Nov. 23–25, 1992).

*Primary Examiner*—Allen J. Robinson
*Attorney, Agent, or Firm*—Burns, Doane, Swecker & Mathis, L.L.P.

[57] ABSTRACT

Agrochemical combinations containing an effective amount of a fungicide having an azole group and an effective amount of an insecticide having a pyrazole, pyrrole or phenylimidazole group; compositions based on each of the two active substances or containing only one of these; and a method for treating plants and seeds in particular to protect them from diseases and insects by applying a combination of the two active substances, are disclosed. The method may include applying a single composition containing both active substances or applying two compositions each containing one of the active substances either at the same time or one after the other to achieve a combined effect.

38 Claims, No Drawings

COMBINATIONS OF A FUNGICIDE CONTAINING AN AZOLE GROUP WITH AN INSECTICIDE CONTAINING A PYRAZOLE, PYRROLE OR PHENYLIMIDAZOLE GROUP This application is a continuation of application Ser. No. 08/640,828, filed Aug. 1, 1996, now abandoned, which is the U.S. national phase of International Application No. PCT/FR94/01254, filed Oct. 27, 1994 and designating the United States.

The present invention relates to new agrochemical combinations for protecting plants comprising both a fungicidal active material and an insecticidal active material and to a process for treating plants using these combinations.

Within the meaning of the present invention, plant is understood to mean a complete plant, a part of the plant or the propagation material of the plant, especially the seed.

More particularly, the subject of the invention is an agrochemical combination for protecting plants against diseases and insects, characterized in that it comprises at least an effective amount of a fungicide containing an azole group (triazole, imidazole) and at least an effective amount of an insecticide other than an organophosphorus, pyrethroid or carbamate insecticide and other than imidacloprid if the fungicide is of benzylideneazolylmethylcycloalkane type.

More advantageously, the subject of the invention is an agrochemical combination for protecting plants against diseases and insects, characterized in that it comprises at least an effective amount of a fungicide of benzylideneazolylmethylcycloalkane type and at least an effective amount of an insecticide containing a pyrazole, pyrrole or phenylimidazole group.

Mention may be made, as benzylideneazolylmethylcycloalkane fungicide, of in particular those described in European Patent Application EP 0,378,953 and preferably 2-(4-chlorobenzylidene)-5,5-dimethyl-1-(1H-1,2,4-triazol-1-ylmethyl)-1-cyclopentanol or triticonazole and 2-(4-chlorobenzylidene)-1-(1H-1,2,4-triazol-1-ylmethyl)-1-cyclohexanol. Triticonazole is moreover known as a fungicide for seed treatment by European Patent Application EP 0,467,791.

Mention may be made, as insecticides containing a pyrazole, pyrrole or phenylimidazole group, of those described by European Patent Applications EP 0,295,117, EP 0,460,940 or EP 0,484,165, respectively. The insecticide chosen in the present invention is preferably chosen from the family of insecticides containing a pyrazole group. The compound whose common name is fipronil, of chemical formula (±)-5-amino-1-(2,6-dichloro-α,α,α-trifluoro-p-tolyl)-4-trifluoromethylsulphinylpyrazole-3-carbonitrile, is advantageously chosen. In addition to its disclosure in European Patent Application EP 0,295,117, the properties of this compound were the subject of a publication in the reports of the Brighton Crop Protection Conference of 1992 (Pest and Diseases, pages 29–34).

Unexpectedly, the combinations according to the invention are better than could have been expected thereof, in the sense that, beyond the simple complementarity of the two compounds, the fungicide, in addition to its own action, acts as a synergist of the insecticide. This is entirely different from the teaching contributed by European Patent Application EP 0,545,834, which discloses the combination of triticonazole with imidacloprid of formula 1-(6-chloro-3-pyridylmethyl)-N-nitroimidazolidin-2-ylideneamine. In fact, in this application, synergy does not occur. Each compound contributes its own specific effectiveness and without harmful interference.

The combinations according to the invention have not shown any more antagonism phenomenon than the abovementioned combination but they have the advantage, with respect to the latter, of being synergistic as regards the insecticidal activity.

Moreover, the combinations according to the invention also have the entirely surprising characteristic that the insecticide acts as a synergist of the fungicide.

It has been found that combinations according to the invention are particularly advantageous for protecting plants against diseases and insects.

The combinations according to the invention can preferably be used for protecting seeds or in soil treatment.

The fungicide is preferably used at a dose ranging from 1 to 1000 g per quintal (g/q) and the insecticide is preferably used at a dose ranging from 5 to 2000 g per quintal of seeds, the fungicide/insecticide ratio is then between 0.0005 and 200 and the insecticide/fungicide ratio is between 0.005 and 2000. The use doses of the combinations of compounds according to the invention can vary within wide limits, especially depending on the virulence of the fungi and the climatic conditions and depending on the nature and the degree of attack by the insects.

Another subject of the invention is compositions comprising an abovementioned combination according to the invention.

The invention additionally comprises a process for treating or protecting plants, and especially the seed, against diseases and insects, characterized in that a combination of the two active materials is applied. It is also possible to apply a composition containing the two active materials or, either simultaneously or successively so as to have the combined effect, two compositions each containing one of the two active materials.

Another subject of the invention is a process for treating seeds, characterized in that the said seed is chosen from the group comprising cereals (wheat, barley, rye), maize, sorghum, sunflower, cotton, rice, peas, rape, potato and market garden crops.

According to a variant, another subject of the invention is a process for soil treatment by application, especially in the sowing furrow:

either of a granule containing the two active materials, in combination or composition, or of a mixture of two granules each containing one of the two active material, optionally with one or a number of agriculturally-acceptable solid or liquid vehicles and/or optionally one or a number of agriculturally-acceptable surface-active agents.

This process is advantageously used in sowing cereals, maize, cotton or sunflower. For cereals and maize, the doses of fungicide are between 1 and 200 g/ha (gram per hectare) and those of insecticide between 10 and 1000 g/ha.

In the case of a treatment of cereal seeds, the doses used will be from 1 to 200 g/q for the fungicide, preferably from 5 to 120 g/q, and from 5 to 150 g/q for the insecticide, preferably from 50 to 100 g/q.

In the case of a treatment of maize or sorghum seeds, the doses used will be from 5 to 150 g/q for the fungicide, preferably from 10 to 100 g/q, and from 25 to 1000 g/q for the insecticide, preferably from 100 to 500 g/q.

In the case of a treatment of sunflower seeds, the doses used will be from 10 to 1000 g/q for the fungicide, preferably from 50 to 200 g/q, and from 50 to 2000 g/q for the insecticide, preferably from 200 to 1000 g/q.

In the case of a treatment of cotton seeds, the doses used will be from 1 to 500 g/q for the fungicide, preferably from 5 to 100 g/q, and from 25 to 1000 g/q for the insecticide, preferably from 100 to 500 g/q.

The process according to the invention is particularly useful for destroying pathogenic fungi and for destroying harmful insects.

Among the latter, the various varieties of flies, such as the wheat bulb fly (*Hylemia coarctata, Phorbia coarctata, Delia coarctata*) or the bean seed fly (*Hylemia platura, Phorbia platura, Delia platura*) as well as the click-beetles (*Agriotes sp., Athous haemorrhoïdalis*), and especially the wireworm, are destroyed entirely satisfactorily by the use of a combination, of a composition or of a treatment according to the invention.

It is advisable, among the pathogenic fungi, to mention especially:

for wheat: *Microdochium nivale, Fusarium roseum, Septoria nodorum, Ustilago sp., Tilletia sp., Puccinia sp., Erysiphe graminis, Septoria tritici* or *Pseudocercosporella herpotrichoïdes;* for barley: *Pyrenophora sp., Fusarium roseum, Microdochium nivale, Ustilago sp., Rhynchosporium secalis, Puccinia hordei* or *Erysiphe graminis;* for rice: *Pyricularia oryzae, Rhizoctonia solani, Helminthosporium oryzae* or *Gibberella fujikuroï;* for maize: *Pythium sp., Fusarium sp., Sphacelotheca reiliana, Colletotrichum sp.* or *Diplodia sp.;* for sorghum: *Fusarium sp., Diplodia natalensis, Colletotrichum sp.* or *Pythium sp.;* for sunflower: *Botrytis cinerea., Sclerotinia sp., Alternaria sp.* or *Phomopsis sp.;* for cotton: *Rhizoctonia solani, Fusarium sp.* or *Pythium sp.;* for peas: *Ascochyta sp., Rhizoctonia sp.* or *Fusarium sp.;* for rape: *Phoma sp., Alternaria sp.* or *Cylindrosporium sp.*

Finally, the invention also relates to the propagation material of plants, and especially the seed, coated with and/or containing a combination as defined above or a composition containing the mixture of two active materials or a mixture of two compositions each contributing one of the two active materials. It is easily understood that the seed especially can be treated either with a composition contributing the fungicide, preferably triticonazole, and then with a composition contributing the insecticide, preferably fipronil, or, conversely, with a composition containing the two active materials.

The term coated with and/or containing means that the active material is mostly found at the surface of the propagation material at the time of application, even though a more or less significant part can enter therein according to the method of application. When the said propagation material is planted out, it absorbs the active material. In fact, commercially it is possible to suggest that most of the active material is at the surface most of the time.

The following examples are given in order to illustrate the combinations, compositions and treatment according to the invention. Of course, these examples are not limiting and many other infestations by insects or by phytopathogenic fungi can be treated by the combinations and compositions according to the invention.

EXAMPLE 1

Wheat seeds were treated according to a conventional seed treatment by coating:

on the one hand, with a suspension concentrate SC containing 600 g/l of Fipronil (0.083 l/q), on the other hand, with a mixture of 0.4 of a suspension concentrate FS containing 300 g/l of triticonazole and of 0.083 l of a suspension concentrate SC containing 600 g/l of Fipronil per quintal of seeds, and finally, with 0.4 l/q of a flowable concentrate for seed treatment (FS) containing 250 g/l of Endosulfan and 100 g/l of Lindane (Remainder SMG FLO®)=Reference.

An untreated part of the seeds is used as control sample.

After having been sown, the wheat seedlings were subjected to an attack by the wheat bulb fly (*Hylemia coarctata*) and the effectiveness of the various treatments is evaluated a few days after this attack. The following results are then obtained:

| Active material | Dose (g/q) | A1 | A1a | B1 | B1a |
|---|---|---|---|---|---|
| Control | 0 | 12.5 | — | 55.8 | — |
| Fipronil | 50 | 11.0 | 12% | 58.5 | 5% |
| Fipronil + Triticonazole | 50 + 120 | 5.8 | 54% | 67.8 | 22% |
| Reference | 100 + 40 | 6.8 | 46% | 64.5 | 16% |

A1=Percentage of plants attacked per plot (10 m$^2$) 64 days after sowing (=DAS).

A1a=Percentage effectiveness with respect to the control, from the formula of Abbot, i.e. (|Control-Treated|/Control) ×100.

B1=Number of plants present per linear meter 64 DAS.

B1a=Gain in number of plants as a percentage with respect to the control, from the formula of Abbot.

EXAMPLE 2

Wheat seeds were treated according to a conventional seed treatment by coating:

on the one hand, with a suspension concentrate SC containing 600 g/l of Fipronil (0.083 l/q), on the other hand, with a mixture of 0.4 l of a suspension concentrate FS containing 300 g/l of triticonazole and of 0.083 l of a suspension concentrate SC containing 600 g/l of Fipronil per quintal of seeds, and finally, with 0.4 l/q of a flowable concentrate for seed treatment (FS) containing 250 g/l of Endosulfan and 100 g/l of Lindane (Remainder SMG FLO®)=Reference.

An untreated part of the seeds is used as control sample.

After having been sown, the wheat seedlings were subjected to an attack by the wheat bulb fly (*Hylemia coarctata*) and the effectiveness of the various treatments is evaluated a few days after this attack. The following results are then obtained:

| Active material | Dose (g/q) | A2 | A2a | B2 | B2a |
|---|---|---|---|---|---|
| Control | 0 | 11.0 | — | 26.47 | — |
| Fipronil | 50 | 4.8 | 56% | 37.85 | 43% |
| Fipronil + Triticonazole | 50 + 120 | 1.8 | 84% | 43.48 | 64% |
| Reference | 100 + 40 | 2.3 | 79% | 41.40 | 56% |

A2=Number of plants attacked per plot (6 m$^2$) 145 DAS.

A2a=Percentage effectiveness with respect to the control, from the formula of Abbot, i.e. (|Control-Treated|/Control) ×100.

B2=Number of plants present per linear meter 91 DAS.

B2a=Gain in number of plants as a percentage with respect to the control, from the formula of Abbot.

EXAMPLE 3

Wheat seeds were treated according to a conventional seed treatment by coating:

on the one hand, with a suspension concentrate SC containing 600 g/l of Fipronil (0.083 l/q), on the other hand, with a mixture of 0.4 l of a suspension concentrate FS containing 300 g/l of triticonazole and of 0.083 l of a suspension concentrate SC containing 600 g/l of Fipronil per quintal of seeds, and finally, with 0.4 l/q of a flowable concentrate for seed treatment (FS) containing 250 g/l of Endosulfan and 100 g/l of Lindane (Remainder SMG FLO®)=Reference.

An untreated part of the seeds is used as control sample.

After having been sown, the wheat seedlings were subjected to an attack by the bean seed fly (*Hylemia platura*) and the effectiveness of the various treatments is evaluated a few days after this attack. The following results are then obtained:

| Active material | Dose (g/q) | A3 | A3a | B3 | B3a | C3 | C3a | D3 | D3a |
|---|---|---|---|---|---|---|---|---|---|
| Control | 0 | 23.8 | — | 8.9 | — | 18.3 | — | 31.5 | — |
| Fipronil | 50 | 23.6 | 0 | 9.4 | 6% | 19.0 | 4% | 34.3 | 9% |
| Fipronil + Triticonazole | 50 + 120 | 31.7 | 33% | 11.0 | 24% | 23.6 | 29% | 46.3 | 47% |
| Reference | 100 + 40 | 35.6 | 50% | 10.6 | 19% | 22.4 | 22% | 49.5 | 57% |

A3=Number of plants present per linear meter 103 DAS.

A3a=Gain in number of plants as a percentage with respect to the control, from the formula of Abbot, i.e. (|Control-Treated|/Control)×100.

B3=Height of the plants in cm 127 DAS.

B3a=Gain in height with respect to the control, from the formula of Abbot.

C3=Height of the plants in cm 152 DAS.

C3a=Gain in height with respect to the control, from the formula of Abbot.

D3=Number of ears present per linear meter 228 DAS.

D3a=Gain in number of ears with respect to the control, from the formula of Abbot.

EXAMPLE 4

Wheat seeds were treated according to a conventional seed treatment by coating:

on the one hand, with a suspension concentrate FS containing 250 g/l of Fipronil (0.2 l/q), on the other hand, with a mixture of 0.4 l of a suspension concentrate FS containing 300 g/l of triticonazole and of 0.2 l of a suspension concentrate FS containing 250 g/l of Fipronil per quintal of seeds, and finally, with 0.4 l/q of a flowable concentrate for seed treatment (FS) containing 250 g/l of Endosulfan and 100 g/l of Lindane (Remainder SMG FLO®)=Reference.

An untreated part of the seeds is used as control sample.

After having been sown, the wheat seedlings were subjected to an attack by the bean seed fly (*Hylemia platura*) and then to an attack by click-beetles (*Athous haemorrhoïdalis*) and the effectiveness of the various treatments is evaluated a few days after these attacks. The following results are then obtained:

| Active material | Dose (g/q) | A4 | A4a | B4 | B4a | C4 | C4a | D4 | D4a |
|---|---|---|---|---|---|---|---|---|---|
| Control | 0 | 30.3 | — | 25.8 | — | 7.6 | — | 572.8 | — |
| Fipronil | 50 | 44.5 | 46% | 2.8 | 89% | 11.6 | 53% | 629.3 | 10% |
| Fipronil + Triticonazole | 50 + 120 | 48.8 | 61% | 1.5 | 94% | 14.8 | 95% | 713.8 | 25% |
| Reference | 100 + 40 | 44.0 | 45% | 2.0 | 92% | 11.3 | 49% | 731.5 | 28% |

A4=Number of plants present per linear meter 50 DAS, after attack by *Hylemia platura*.

A4a=Gain in number of plants as a percentage with respect to the control, from the formula of Abbot, i.e. (|Control-Treated|/Control)×100.

B4=Percentage of plants attacked by click-beetles (*Athous haemorrhoïdalis*) per plot (6.25 m$^2$) 99 DAS.

B4a=Percentage effectiveness of the treatment with respect to the control, from the formula of Abbot.

C4=Height of the plants in cm 134 DAS.

C4a=Gain in height with respect to the control, from the formula of Abbot.

D4=Number of ears present per linear meter 228 DAS.

D4a=Gain in number of ears with respect to the control, from the formula of Abbot.

Moreover, no phytotoxicity phenomenon is observed in Examples 1 to 4.

These examples illustrate equally well the superiority of the combinations, compositions and processes according to the invention both with respect to the insecticide alone and with respect to a commercial reference product.

EXAMPLE 5

In vivo test of the combination of fipronil with triticonazole on *Microdochium nivale* (responsible for snow mould of wheat) by seed treatment:

Aqueous suspensions of the products, alone or as mixtures in the triticonazole/fipronil ratios equal to 1, 0.5, 0.2, 0.1 and 0.05, are prepared.

Hard wheat seeds, naturally infected, are treated by means of these suspensions according to a conventional seed treatment by coating.

The seeds are dried at 20° C. for 24 hours.

After having been sown, the seeds are placed in a humid atmosphere at 5° C. for 15 days and then transferred to 10° C. for one week.

Reading is carried out by counting the number of healthy seedlings and a percentage effectiveness, by comparison with the control (wheat resulting from infected and untreated seeds), is calculated.

The results are collated in the table below.

| Active material | Dose (g/100 kg) | Effectiveness (%) |
|---|---|---|
| Triticonazole | 5 | 36 |
| Triticonazole + Fipronil | 5 + 5 | 50 |
|  | 5 + 10 | 57 |
|  | 5 + 25 | 55 |
|  | 5 + 50 | 53 |
|  | 5 + 100 | 66 |

EXAMPLE 6

In vivo test of the combination of fipronil with triticonazole on *Pyrenophora graminea* (responsible for leaf stripe of barley) by seed treatment:

Aqueous suspensions of the products, alone or as mixtures in the triticonazole/fipronil ratios equal to 0.5, 0.2 and 0.1, are prepared.

Barley seeds, naturally infected, are treated by means of these suspensions according to a conventional seed treatment by coating.

The seeds are dried at 20° C. for 24 hours.

After having been sown, the seeds are placed in a humid atmosphere at 5° C. for 15 days, then transferred to 10° C. for one week and then to 20° C. for 3 weeks.

Reading is carried out by counting the number of healthy seedlings and a percentage effectiveness, by comparison with the control (barley resulting from infected and untreated seeds), is calculated.

The results are collated in the table below.

| Active material | Dose (g/100 kg) | Effectiveness (%) |
|---|---|---|
| Triticonazole | 5 | 55 |
| Triticonazole + Fipronil | 5 + 10 | 63 |
|  | 5 + 25 | 74 |
|  | 5 + 50 | 76 |

EXAMPLE 7

In vivo test of the combination of fipronil with triticonazole on *Puccinia recondita* special form tritici (responsible for brown rust of wheat) by seed treatment:

Aqueous suspensions of the products, alone or as mixtures in the triticonazole/fipronil ratios equal to 1, 0.5, 0.2, 0.1 and 0.05, are prepared.

Soft wheat seeds are treated by means of these suspensions according to a conventional seed treatment by coating.

The seeds are dried at 20° C. for 24 hours.

After having been sown, the seeds are placed in a humid atmosphere at 10° C. until the two-leaf stage, alternatively defined by Stage 12 according to the Zadoks scale. This scale is defined in the "revue Phytiatrie phytopharmacie", No. 26, pages 129–140, 1977.

The plants are then infected with an aqueous suspension containing 100,000 spores of *Puccinia recondita* per ml.

The plants are then placed for 24 hours at 20° C. in an atmosphere at 100% relative humidity and then at 20° C. in an atmosphere at 70% relative humidity for 10 days.

Reading is carried out by evaluating the percentage of leaf surface infected for each of the 2 leaves, and a percentage effectiveness, by comparison with the control (infected and untreated wheat seedlings), is calculated: i.e. F1 for the first leaf and F2 for the second leaf.

The results are collated in the table below.

| Active material | Dose (g/100 kg) | F1 (%) | F2 (%) |
|---|---|---|---|
| Triticonazole | 5 | 74 | 42 |
| Triticonazole + Fipronil | 5 + 5 | 100 | 100 |
|  | 5 + 10 | 100 | 99 |
|  | 5 + 25 | 100 | 100 |
|  | 5 + 50 | 100 | 100 |
|  | 5 + 100 | 100 | 100 |

EXAMPLE 8

In vivo test of the combination of fipronil with triticonazole on *Fusarium culmorum* (responsible for stalk rot and root rot of maize) by seed treatment:

Aqueous suspensions of the products, alone or as a mixture in the triticonazole/fipronil ratio equal to 0.01, are prepared.

Soft maize seeds are treated by means of this suspension according to a conventional seed treatment by coating.

The seeds are dried at 20° C. for 24 hours.

After having been sown, the seeds are infected with an aqueous suspension containing 500,000 spores of *Fusarium culmorum* per ml, then placed in a humid atmosphere at 10° C. for 21 days and then transferred to 15° C. for 2 weeks.

Reading is carried out by counting the number of healthy seedlings and a percentage effectiveness, by comparison with the control (maize resulting from infected and untreated seeds), is calculated.

The results are collated in the table below.

| Active material | Dose (g/100 kg) | Effectiveness (%) |
|---|---|---|
| Triticonazole | 1.25 | 32 |
| Triticonazole + Fipronil | 1.25 + 125 | 44 |

Examples 5 to 8 clearly illustrate the superiority of the combinations, compositions and processes according to the invention with respect to the fungicide alone.

Moreover, no phytotoxicity phenomenon is observed in these examples.

For their practical use, the combinations according to the invention are rarely used alone and can be used in compositions containing one or the other of the active materials or alternatively the two together. In each composition, the active materials are generally used in combination with a solid or liquid vehicle which can be used in agriculture and optionally at least one surface-active agent.

These compositions, which can be used for protecting plants against fungal diseases and/or against insects, contain, as active material, at least one of the constituents of the combination according to the invention as described above in combination with solid or liquid vehicles which are acceptable in agriculture and/or surface-active agents which are also acceptable in agriculture. In particular, the inert and conventional vehicles and the conventional surface-active agents can be used.

These compositions generally contain between 0.5 and 95% of compound according to the invention, that is to say either the combination or one of the two active materials.

In the present account, the term "vehicle" denotes a natural or synthetic, organic or inorganic material with which the active material is combined to facilitate its application on the plant, on seeds or on the ground. This vehicle is thus generally inert and must be agriculturally acceptable, especially on the treated plant. The vehicle can be solid (clays, natural or synthetic silicates, silica, resins, waxes, solid fertilizers and the like) or liquid (water, alcohols, ketones, petroleum fractions, aromatic or paraffinic hydrocarbons, chlorinated hydrocarbons, liquefied gases, and the like).

The surface-active agent can be an emulsifying, dispersing or wetting agent of ionic or nonionic type. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (especially alkylphenols or arylphenols), salts of esters of sulphosuccinic acids, taurine derivatives (especially alkyltaurates), or phosphoric esters of polyoxyethylated phenols or alcohols. The presence of at least one surface-active agent is generally indispensable when the active material and/or the inert vehicle are not soluble in water and when the carrier agent of the application is water.

These compositions can also contain all kinds of other ingredients such as, for example, protective colloids, adhesives, thickening agents, thixotropic agents, penetrating agents, stabilizing agents, sequestering agents and the like, as well as other known active materials possessing pesticidal properties (especially insecticides or fungicides) or possessing properties promoting plant growth (especially fertilizers) or possessing plant growth regulatory properties. More generally, the compounds according to the invention can be combined with all the solid or liquid additives corresponding to the conventional formulating techniques.

For their application, the constituents of the combination are therefore often found in the form of compositions, which are themselves in fairly diverse solid or liquid forms.

There may be mentioned, as solid composition forms, powders for dusting or dispersion (with a content of combination according to the invention which can range up to 100%) and granules, especially those obtained by extrusion, by compacting, by impregnation of a granulated vehicle, or by granulation from a powder (the content of combination according to the invention in these granules being between 0.5% and 80% for the latter cases).

According to an example of a granules composition, the following constituents are used:

G Example combination or one of the two active material 50 g epichlorohydrin 2.5 g polyglycol cetyl ether 2.5 g polyethylene glycol 35 g kaolin (particle size: 0.3 to 0.8 mm) 910 g In this specific case, the active materials are mixed with the epichlorohydrin, the mixture is dissolved in 60 g of acetone and the polyethylene glycol and the polyglycol cetyl ether are then added. The kaolin is sprinkled with the solution obtained and the acetone is then evaporated under vacuum. Such a microgranule is advantageously used to control soil fungi.

The compounds or combinations of the said compounds can also be used in the form of powders for dusting. It is also possible to use a composition comprising 50 g of active material(s) and 950 g of talc or it is also possible to use a composition comprising 20 g of active material(s), 10 g of finely divided silica and 970 g of talc. These constituents are mixed and milled and the mixture is applied by dusting.

There may be mentioned, as liquid composition forms or forms intended to constitute liquid compositions at the time of application, solutions, in particular water-soluble concentrates, emulsifiable concentrates, emulsions, suspension concentrates, aerosols, wettable powders (or powder to be sprayed) or pastes.

The emulsifiable or soluble concentrates most often comprise 10 to 80% of active material while the emulsions or solutions ready for application contain 0.01 to 20% of active material.

For example, in addition to the solvent, the emulsifiable concentrates can contain, when necessary, 2 to 20% of suitable additives, such as the abovementioned stabilizing agents, surface-active agents, penetrating agents, corrosion inhibitors, dyes or adhesives.

The suspension concentrates, also applicable by spraying, are prepared so as to obtain a stable fluid product which does not settle out and they generally contain from 2 to 75% of active material, from 0.5 to 15% of surface-active agents, from 0.1 to 10% of thixotropic agents, from 0 to 10% of suitable additives, such as antifoaming agents, corrosion inhibitors, stabilizing agents, penetrating agents and adhesives, and, as vehicle, water or an organic liquid in which the active material is insoluble or nearly insoluble. Certain organic solid materials or inorganic salts can be dissolved in the vehicle to aid in preventing sedimentation or as antifreezes for water.

An example of such a formulation is given below:

SC Example active material 600 g polyethoxylated tristyrylphenyl phosphate 50 g polyethoxylated alkylphenol 50 g sodium polycarboxylate 20 g ethylene glycol 50 g organopolysiloxane oil (antifoaming agent) 1 g polysaccharide 1.5 g water q.s. for 11

Wettable powders (or powders to be sprayed) are generally prepared so that they contain 20 to 95% of active material, and they generally contain, in addition to the solid vehicle, from 0 to 5% of a wetting agent, from 3 to 10% of a dispersing agent and, when necessary, from 0 to 10% of one or more stabilizing agents and/or other additives, such as penetrating agents, adhesives, or anticlumping agents, dyes, and the like.

To obtain these powders to be sprayed or wettable powders, the active materials are intimately mixed, in suitable mixers, with the additional substances and the mixture is milled with mills or other suitable grinders. Powders to be sprayed are thereby obtained with advantageous wettability and suspensibility. They can be suspended in water at any desired concentration.

Pastes can be produced in place of wettable powders. The conditions and modes of production and use of these pastes are similar to those of wettable powders or powders to be sprayed.

As has already been said, aqueous dispersions and emulsions, for example the compositions obtained by diluting a wettable powder or an emulsifiable concentrate according to the invention with water, are contained within the general scope of the present invention. The emulsions can be of the water-in-oil or oil-in-water type and they can have a thick consistency, like that of a "mayonnaise".

We claim:

1. An agrochemical combination for protecting plants against fungal disease and insects, said combination comprising, in synergistic combinatory amount:
    (a) a fungicidally effective amount of triticonazole; and
    (b) an insecticidally effective amount of fipronil;
the triticonazole: fipronil weight ratio being between 0.0005 and 200.

2. A combination according to claim 1, wherein triticonazole is a synergist of fipronil.

3. A combination according to claim 1, wherein fipronil is a synergist of triticonazole.

4. An agrochemical composition comprising:
    (a) in synergistic combinatory amount:
        (i) a fungicidally effective amount of triticonazole; and
        (ii) an insecticidally effective amount of fipronil;
        the triticonazole: fipronil weight ratio being between 0.0005 and 200;
    and
    (b) an agriculturally acceptable liquid of solid vehicle.

5. A composition according to claim 4, further comprising an agriculturally acceptable surface-active agent.

6. A composition according to claim 4, wherein triticonazole is a synergist of fipronil.

7. A composition according to claim 4, wherein fipronil is a synergist of triticonazole.

8. A process for protecting plants against fungal disease and insects, said process comprising applying to said plants or to the locus in which they grow, in synergistic combinatory amount:
    (a) a fungicidally effective amount of triticonazole; and
    (b) an insecticidally effective amount of fipronil;
the triticonazole: fipronil weight ratio being between 0.0005 and 200.

9. A process according to claim 8, comprising treating plant seed.

10. A process according to claim 8, comprising treating the soil.

11. A composition according to claim 4, comprising between 0.5% and 95% of triticonazole and fipronil combined.

12. A composition according to claim 5, comprising between 0.5% and 95% of triticonazole and fipronil combined.

13. A process according to claim 8, wherein triticonazole and fipronil are applied simultaneously.

14. A process according to claim 8, wherein triticonazole and fipronil are applied successively.

15. A process according to claim 9, wherein the dose of triticonazole is between 1 and 1000 g per quintal of seed, and the dose of fipronil is between 5 and 2000 g per quintal of seed.

16. A process according to claim 9, wherein the seed is cereal seed.

17. A process according to claim 16, wherein the seed is wheat, barley or rye seed.

18. A process according to claim 9, wherein the seed is maize or sorghum seed.

19. A process according to claim 9, wherein the seed is sunflower seed.

20. A process according to claim 9, wherein the seed is cotton seed.

21. A process according to claim 9, wherein the seed is rice seed.

22. A process according to claim 16, wherein the dose of triticonazole is from 1 to 200 g per quintal of seed, and the dose of fipronil is from 5 to 150 g per quintal of seed.

23. A process according to claim 22, wherein the dose of triticonazole is from 5 to 120 g per quintal of seed, and the dose of fipronil is from 50 to 100 g per quintal of seed.

24. A process according to claim 18, wherein the dose of triticonazole is from 5 to 150 g per quintal of seed, and the dose of fipronil is from 25 to 1000 g per quintal of seed.

25. A process according to claim 24, wherein the dose of triticonazole is from 10 to 100 g per quintal of seed, and the dose of fipronil is from 100 to 500 g per quintal of seed.

26. A process according to claim 19, wherein the dose of triticonazole is from 10 to 1000 g per quintal of seed, and the dose of fipronil is from 50 to 2000 g per quintal of seed.

27. A process according to claim 26, wherein the dose of triticonazole is from 50 to 200 g per quintal of seed, and the dose of fipronil is from 200 to 1000 g per quintal of seed.

28. A process according to claim 20, wherein the dose of triticonazole is from 1 to 500 g per quintal of seed, and the dose of fipronil is from 25 to 1000 g per quintal of seed.

29. A process according to claim 28, wherein the dose of triticonazole is from 5 to 100 g per quintal of seed, and the dose of fipronil is from 100 to 500 g per quintal of seed.

30. A process according to claim 13, wherein triticonazole and fipronil are applied in the form of an agrochemical composition comprising:
    (a) in synergistic combinatory amount:
        (i) a fungicidally effective amount of triticonazole; and
        (ii) an insecticidally effective amount of fipronil;
        the triticonazole: fipronil weight ratio being between 0.0005 and 200;
    and
    (b) an agriculturally acceptable liquid or solid vehicle.

31. A process according to claim 10, wherein the soil is treated in the sowing furrow.

32. A process according to claim 10, wherein triticonazole and fipronil are applied in the form of granules.

33. A process according to claim 32, wherein the soil is for growing maize or cereal, the dose of triticonazole is between 1 and 200 g/ha and the dose of fipronil is between 10 and 1000 g/ha.

34. A propagation material of plants, wherein the material comprises, in synergistic combinatory amount:
    (a) a fungicidally effective amount of triticonazole; and
    (b) an insecticidally effective amount of fipronil;
    the triticonazole: fipronil weight ratio being between 0.0005 and 200.

35. A propagation material according to claim 34, wherein the material is plant seed.

36. A propagation material according to claim 35, wherein the seed is coated with the triticonazole and fipronil.

37. A propagation material according to claim 35, wherein the seed comprises between 1 to 1000 g of triticonazole and between 5 and 2000 g of fipronil per quintal.

38. A propagation material according to claim 36, wherein the seed is coated with between 1 and 1000 g of triticonazole and between 5 and 2000 g of fipronil per quintal.

* * * * *